(12) United States Patent
Kawai et al.

(10) Patent No.: US 8,127,594 B2
(45) Date of Patent: Mar. 6, 2012

(54) GAS SENSOR

(75) Inventors: Takeshi Kawai, Komaki (JP); Kentaro Mori, Inuyama (JP); Ryohei Aoki, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 419 days.

(21) Appl. No.: 12/496,702

(22) Filed: Jul. 2, 2009

(65) Prior Publication Data

US 2010/0000293 A1 Jan. 7, 2010

(30) Foreign Application Priority Data

Jul. 4, 2008 (JP) .................................. 2008-175374
Apr. 24, 2009 (JP) .................................. 2009-105826

(51) Int. Cl.
*G01N 7/00* (2006.01)
(52) U.S. Cl. ..................... 73/31.05; 73/23.31
(58) Field of Classification Search ................. 73/31.05, 73/23.31; 204/426, 428, 429
See application file for complete search history.

(56) References Cited

U.S. PATENT DOCUMENTS 7,771,576 B2 * 8/2010 Mizutani et al. .............. 204/424
7,811,434 B2 * 10/2010 Mizutani et al. .............. 204/426
2008/0016942 A1 1/2008 Mizutani et al.

FOREIGN PATENT DOCUMENTS

JP 61-134655 A 6/1986
JP 2008-046112 A 2/2008

* cited by examiner

*Primary Examiner* — Hezron E Williams
*Assistant Examiner* — Rodney T Frank
(74) *Attorney, Agent, or Firm* — Sughrue Mion, PLLC

(57) ABSTRACT

A gas sensor including: a gas sensing element including first and second ceramic layers. The first ceramic layer has a first through hole and a first through hole conductor covering an inner surface thereof. The first ceramic layer includes a first conductor which includes: a first peripheral conductive portion electrically connected to the first through hole conductor; a first lead portion that is narrower than the first peripheral conductive portion; and a first contact conductive portion that is wider than the first lead portion. The first peripheral conductive portion, the first lead portion and the first contact conductive portion are integrally formed and arranged in this order in a longitudinal direction. The second ceramic layer includes a second conductor electrically connected to at least the first contact conductive portion.

9 Claims, 8 Drawing Sheets

GAS SENSOR

BACKGROUND OF THE INVENTION

1. Field of the Invention

The present invention relates to a gas sensor including a stacked-type gas sensor including a plurality of stacked ceramic layers.

2. Description of the Related Art

A plate-shaped gas sensor including a plurality of stacked ceramic layers (solid electrolyte layers) and provided with an electrode (a sensing portion) on a leading end side thereof is known. Such a gas sensor generally includes a ceramic layer having an electrode formed on one surface thereof and a lead portion formed on an opposite side surface thereof, where the electrode and the lead portion are electrically interconnected by means of a through hole conductor formed in a through hole (a penetration hole) penetrating through the ceramic layers (see JP-A-61-134655).

The ceramic layers (solid electrolyte layers) are formed of green sheets. As shown in FIG. 11, after a through hole 241$h$1 is bored in a ceramic layer 241, an unsintered through hole conductor 206 is formed on an inner peripheral surface of the through hole 241$h$1, and an unsintered peripheral conductive portion 206S is formed at a periphery of the through hole 241$h$. Similarly, after a through hole 221$h$1 is bored in a ceramic layer 221 opposing the ceramic layer 241, an unsintered through hole conductor 226 is formed on an inner peripheral surface of the through hole 221$h$1, and an unsintered peripheral conductive portion 226S is additionally formed at a periphery of the through hole 221$h$1.

The ceramic layers 221 and 241 are stacked in such a way that the peripheral conductive portions 206S and 226S of the respective ceramic layers 221 and 241 contact one another, and are thereby electrically connected.

The ceramic green sheet and the unsintered metalized layer differ from each other in the amount of sintering shrinkage. For this reason, deformation, such as warpage in the peripheral conductive portions 206S and 226S, may occur during a sintering operation, and a clearance CL may be generated between opposing members, which results in a deterioration of electrical connection reliability. In this regard, a technique is disclosed for providing elongated conductive portions 247, 222 extending from the respective peripheral conductive portions 206S and 226S to surfaces of the respective ceramic layer 221 and 241 and for establishing electrical connection between the elongated conductive portions 247, 222 which are not subject to warpage (which are not subject to the clearance CL between opposing members) (see JP-A-2008-46112).

Since the cost of conductive materials, such as noble metals, has recently increased, providing the elongated conductive portions 247, 222 as described in JP-A-2008-46112 results in an increase in the amount of conductive material that is used. In FIG. 11, the elongated conductive portions 247 and 222 contact each other (are electrically connected). However, although it is enough to provide electrical conduction between the elongated conductive portions 247 and 222 and the respective peripheral conductive portions 206S and 226S, conductive materials are wastefully used in the elongated conductive portions 247 and 222 shown in FIG. 11.

Also, since the elongated conductive portions contain components different from that of the ceramic layers, adhesion between adjacent ceramic layers may decrease as the portion of the elongated conductive portions increases.

SUMMARY OF THE INVENTION

The invention was made in consideration of the above noted problems of the prior art, and an object thereof is to provide a gas sensor including a conductor which exhibits higher electrical connection reliability with another conductor, which allows for a reduction in the amount of conductive material that is used, and which also enhances adhesion between ceramic layers.

The above objects have been achieved by providing, in a first aspect of the invention, a gas sensor comprising: a plate-shaped gas sensing element extending in a longitudinal direction and comprising a sensing portion provided at a leading-end side in the longitudinal direction, the gas sensing element comprising a plurality of stacked ceramic layers including a first ceramic layer having a first surface and a second ceramic layer having a second surface opposing the first surface, wherein the first ceramic layer has a first through hole, a first through hole conductor covering at least an inner surface of the first through hole, wherein the first ceramic layer comprises a first conductor formed on the first surface thereof, wherein the first conductor comprises: a first peripheral conductive portion provided at a periphery of the first through hole and electrically connected to the first through hole conductor; a first lead portion that is narrower than the first peripheral conductive portion; and a first contact conductive portion that is wider than the first lead portion, wherein the first peripheral conductive portion, the first lead portion and the first contact conductive portion are integrally formed and arranged in this order in the longitudinal direction, and wherein the second ceramic layer comprises a second conductor formed on the second surface thereof and electrically connected to at least the first contact conductive portion.

In this configuration, the first contact conductive portion of the first conductor is electrically connected to the second conductor. The essential requirement for the first lead portion provided between the first peripheral conductive portion and the first contact conductive portion is to establish electrical conduction between the first peripheral conductive portion and the first contact conductive portion. Therefore, since the first lead portion is provided with a narrow width, the amount of conductive material used can be reduced when compared with a case where the entirety of the first conductor is provided with a given width. Moreover, when the first lead portion is provided with a narrow width, an exposed area of the first ceramic layer having no first conductor is increased. Consequently, adhesion between the first ceramic layer and the second ceramic layer opposing each other is enhanced.

Further, since the first contact conductive portion having a relatively greater area is located away from the first peripheral conductive portion provided at a periphery of the through hole that is likely to deform during a sintering process, the reliability of electrical connection with the second conductor is enhanced.

In a preferred implementation, the second ceramic layer may have a second through hole with a second through hole conductor covering at least an inner surface of the second through hole, the second through hole being connected to the first through hole, wherein the second conductor comprises: a second peripheral conductive portion provided at a periphery of the second through hole and electrically connected to the second through hole conductor; a second lead portion that is narrower than the second peripheral conductive portion; and a second contact conductive portion that is wider than the second lead portion, wherein the second peripheral conductive portion, the second lead portion and the second contact conductive portion may be integrally formed and arranged in this order in the longitudinal direction, and wherein at least the first contact conductive portion and the second contact conductive portion are electrically connected to each other.

In this configuration, the second lead portion of the second conductor opposing the first conductor is also narrowed similar to the first lead portion. As in the case of the first conductor, the amount of conductive material used is reduced, and adhesion between the first ceramic layer and the second ceramic layer is enhanced.

In another preferred implementation, the first lead portion and/or a second lead portion comprises a plurality of separated conductors extending in the longitudinal direction and electrically connecting the first peripheral conductive portion and the first contact conductive portion.

In this configuration, a plurality of first lead portions and/or a plurality of second lead portions are provided. Hence, even when one of the lead portions is broken, electrical conduction is maintained by the other of the lead portions. Consequently, the reliability of electrical connection is further enhanced.

In yet another preferred implementation, the first contact conductive portion and/or the second contact conductive portion has a loop shape.

In this configuration, even when the amount of conductive material used for the first and second contact conductive portions is kept constant, the outer dimensions of the first and second contact conductive portions can be increased. Therefore, even when a slight misalignment has occurred at a stacking process of the ceramic layers, the first and second contact conductive portions can reliably contact their opposing conductors.

In yet a further preferred implementation, the first contact conductive portion has a larger area than that of the first peripheral conductive portion, and/or the second contact conductive portion has an area larger than that of the second peripheral conductive portion.

As a result, the reliability of electrical connection of the first conductor or the second conductor is further enhanced.

Moreover, even when the first ceramic serving as a main component of the first ceramic layer is different from a material of the second ceramic serving as a main component of the second ceramic layer which may decrease adhesion between the first and second ceramic layers, exposed areas of the first and second ceramic layers are increased by providing the first and second lead portions having narrow widths. Consequently, adhesion is enhanced. As used herein, the term "main component" means a component contained in an amount of 50 mass % or more.

According the above-described aspect of the invention, the gas sensor includes conductors which can exhibit higher electrical connection reliability, which can lead to a further reduction in the amount of conductive material that is used, and which can also enhance adhesion between ceramic layers.

DETAILED DESCRIPTION OF THE PREFERRED EMBODIMENTS

An embodiment of the present invention will next be described with reference to the drawings. However, the present invention should not be construed as being limited thereto.

Figure 1:
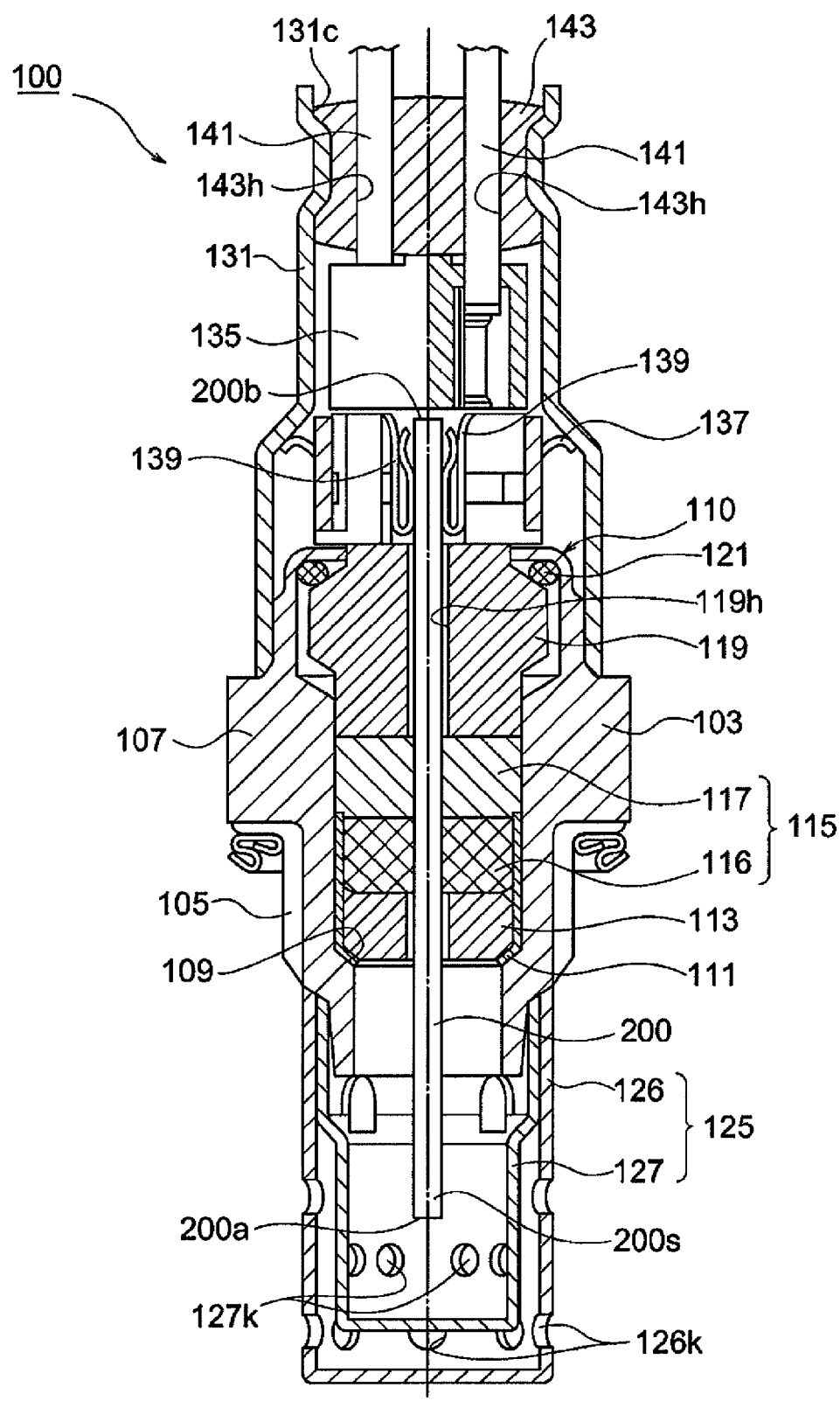
FIG. 1 is a cross-sectional view showing the configuration of an oxygen sensor (a gas sensor) of an embodiment of the present invention.

FIG. 1 shows an oxygen sensor (a gas sensor) 100 of an embodiment of the present invention. The oxygen sensor 100 is mounted on an exhaust pipe (not shown) of an automobile and senses the concentration of oxygen in an exhaust gas. In the embodiment, a downward direction in FIG. 1 (a direction of a protector 125) is taken as a leading-end side of the oxygen sensor 100, and an upward direction in the same is taken as a base end of the oxygen sensor.

The oxygen sensor 100 includes a gas sensing element 200, a cylindrical metal shell 103 holding the gas sensing element 200 therein, a protector 125 mounted at a predetermined position on the leading-end side of the metal shell 103, an outer cylinder 131 connected to the predetermined portion on a base-end side of the metal shell 103, and the like.

The gas sensing element 200 is an elongated, plate-shaped, stacked-type element that has a leading end 200a and a base end 200b and that includes a plurality of stacked ceramic layers, and is provided with a sensing portion 200s (described below) in a leading end portion thereof. A dimension of the gas sensing element 200 of the present embodiment is about 40 mm in length×about 5 mm in width×about 1.2 mm in thickness.

The metal shell 103 contains stainless steel such as SUS430. The metal shell 103 includes, in an outer surface thereof, an external thread portion 105 used for mounting the gas sensor 100 on the exhaust pipe and a hexagonal engagement portion 107 for engaging a tool during a mounting operation. The metal shell 103 includes, in an inner surface thereof, an inner step portion 109 inwardly protruding in a radial direction, so as to support a cylindrical metal holder 111 from an outside thereof. The metal holder 111 holds the gas sensing element 200.

In the metal holder 111, a ceramic holder 113 and a talc-filled layer 115 for positioning the gas sensing element 200 at a predetermined position are arranged in this order from the leading-end side. The talc-filled layer 115 includes, in the order from its leading-end side, a first talc-filled layer 116 and a second talc-filled layer 117. A cylindrical shaped multistage sleeve 119 containing alumina is disposed on a base end of the second talc-filled layer 117. The gas sensing element 200 is inserted into the ceramic holder 113, the talc-filled layer 115, and an axial hole 119h of the sleeve 119. The metal shell 103 includes a crimping portion 110 extending along a base end of the metal shell 103 so as to cover a base end of the sleeve 119. The sleeve 119 is pressed against the leading-end side of the metal shell 103 through a stainless-steel ring member 121, by inwardly folding the crimping portion 110, whereby the gas sensing element 200 is clamped and held by the ceramic holder 113, the talc-filled layer 115, and the like.

The metal protector 125 is welded to an outer periphery of the leading end of the metal shell 103 so as to protrude from the leading end of the metal shell 103 and cover the sensing portion 200s of the gas sensing element 200. The protector 125 has a double structure including an outer protector 126 and an inner protector 127 provided inside the outer protector 126. Each of the outer protector 126 and the inner protector 127 is formed into a bottomed cylindrical shape having its leading end closed. The outer protector 126 has a plurality of gas introduction holes 126k which allow for introduction of exhaust gas from an outside to an inside thereof, and the inner protector 127 has a plurality of gas introduction holes 127k allowing for introduction of exhaust gas from an outside thereof to an inside thereof.

The outer cylinder 131 is welded to an outer peripheral surface of the base end side of the metal shell 103, and a cylindrical separator 135 is arranged in the outer cylinder 131. The separator 135 has insertion holes for separately holding a plurality of lead wires 141 and a center hole for housing a base end of the gas sensing element 200 on the leading-end side of the separator 135. A plurality of connector fittings 139 are arranged so as to surround the center hole of the separator 135, and the connector fittings 139 are electrically connected to a terminal portions provided on the base end of the gas sensing element 200. The lead wires 141 extending from the respective connector fittings 139 are drawn out from a base end side of the gas sensor 100. A cylindrical spring-shaped holding member 137 extends radially outward and is disposed along an outer periphery of a leading end of the separator 135. The holding member 137 extends radially outward so as to contact an inner surface of the outer cylinder 131, whereby the separator 135 is fixed.

A columnar rubber cap 143 is disposed on a base end of the separator 135 so as to close a base-end opening 131c of the outer cylinder 131. An outer periphery of the outer cylinder 131 is crimped inwardly in the radial direction while the rubber cap 143 remains attached to the outer cylinder 131, whereby the rubber cap 143 is fixed to the outer cylinder 131. A plurality of insertion holes 143h for inserting the lead wires 141 is formed in the rubber cap 143.

The the gas sensing element 200 will now be described by reference to FIG. 2. In the present embodiment, the gas sensing element 200 includes a plurality of stacked ceramic layers 241, 221, 231 and 211 (which respectively correspond to a protective layer, a second solid electrolyte layer, an insulation layer, and a first solid electrolyte layer in FIG. 2). Through holes are used to establish electrical conduction among the ceramic layers 241, 221, 231 and 211.

Figure 2:
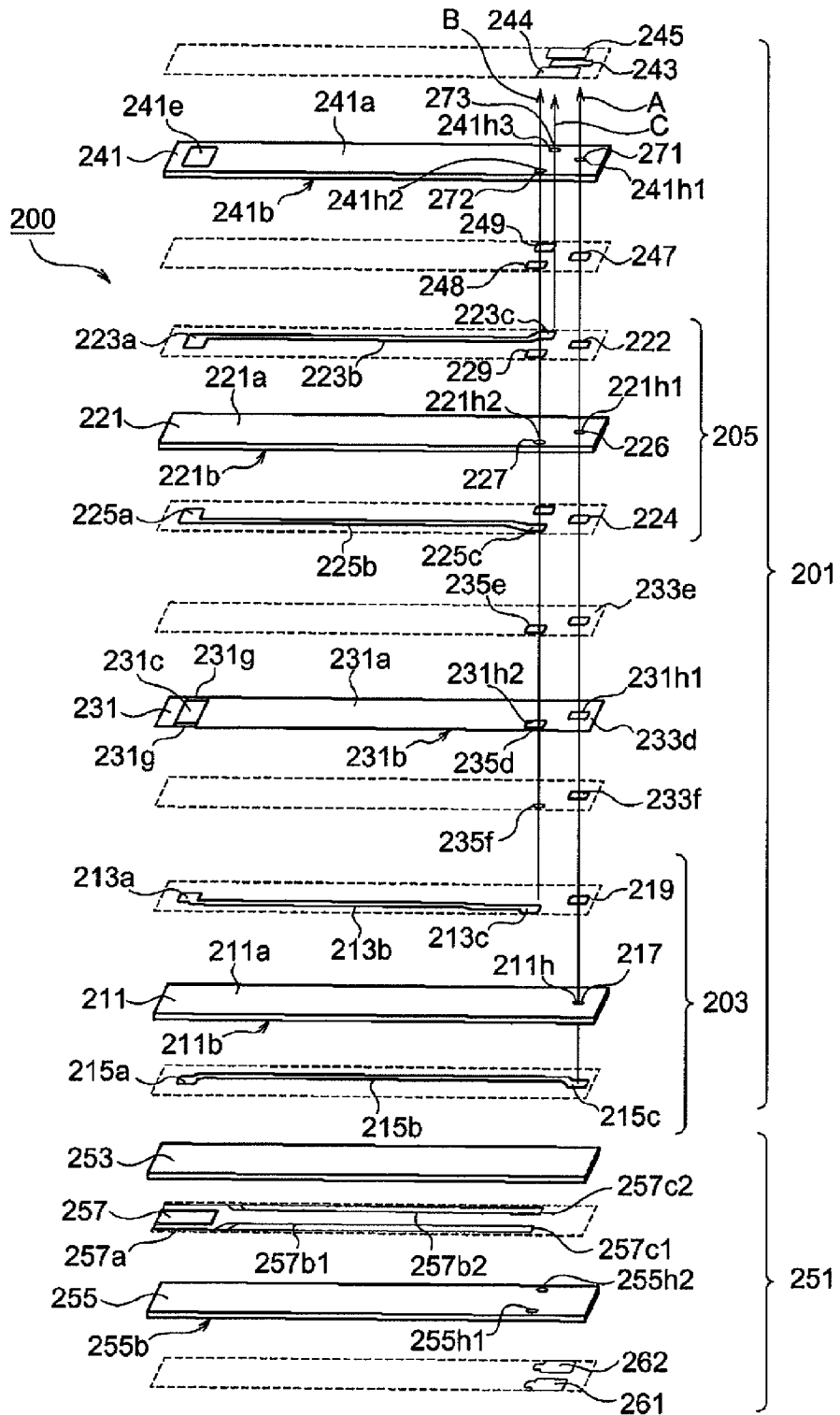
FIG. 2 is an exploded perspective view showing the configuration of a gas sensor.

In FIG. 2, an arrow A denotes a through hole along line A for establishing electrical conduction from a connection portion 215c of a second electrode 215a formed on the first solid electrolyte layer 211 to a first electrode pad 243 formed on the protective layer 241. Likewise, an arrow B denotes a through hole along line B for establishing electrical conduction from a connection portion 213c of a first electrode 213a formed on the first solid electrolyte layer 211 to a second electrode pad 244 formed on the protective layer 241.

An arrow C denotes a through hole along line C for establishing electrical conduction from a connection portion 223c of a third electrode 223a formed on the second solid electrolyte layer 221 to a third electrode pad 245 formed on the protective layer 241.

The electrode pads 243 to 245 are connected to the respective connector fittings 139 provided on the gas sensor main body (see FIG. 1).

In the present embodiment, conductors 247, 222 provided corresponding to respective through holes of the protective layer 241 and the second solid electrolyte layer 221 opposing each other are, for example, formed to have a specific shape, whereby electrical connection reliability achieved when the layers are superimposed one on top of the other is enhanced, and the amount of conductive material that is used is reduced. However, a specific configuration of the conductor will be described below.

First, the overall configuration of the gas sensing element 200 is described. The gas sensing element 200 includes a sensor portion 201 configured to sensing the concentration of oxygen and a heater 251 for heating the sensor portion 201. The sensor portion 201 includes an oxygen concentration detection cell 203 and an oxygen pump cell 205. A left side of FIG. 2 (a side on which the first electrode 213a and the second electrode 215a are situated) corresponds to a leading end side of the gas sensing element 200, and a right side thereof is a base end side.

The oxygen concentration detection cell 203 includes the first solid electrolyte layer 211 containing a sintered partially-stabilized zirconia element, a first electrode 213a formed in a leading-end side portion of a front surface 211a of the first solid electrolyte layer, and a second electrode 215a formed in a leading-end side portion of a back surface 211b of the first solid electrolyte layer.

A lead portion 213b and a substantially-oblong connection portion 213c are integrally formed, in this order, from the first electrode 213a toward its base end along a longitudinal direction of the gas sensing element 200. In addition, a lead portion 215b and a substantially-oblong connection portion 215c are integrally formed, in this order, from the second electrode 215a toward its base end along a longitudinal direction of the gas sensing element 200.

Accordingly, the oxygen concentration detection cell 203 is formed to include the second electrode 215a functioning as a reference electrode and the first electrode 213a functioning as a sensing electrode.

An insulation layer 231 containing alumina as a main component thereof is stacked on the front surface 211a of the oxygen concentration detection cell 203. A rectangular gas measurement chamber 231c is opened in the leading-end side portion of the insulation layer 231, whereby the first electrode 213a is exposed in the gas measurement chamber 231c. A diffusion rate control portion 231g is provided at each of opposing edges of the gas measurement chamber 231c extending in a longitudinal direction of the insulation layer 231 along edges of the gas measurement chamber 231c, and a detection gas flows in and out of the gas measurement chamber 231c through the diffusion rate control portions 231g.

Through holes of the first solid electrolyte layer 211 will now be described. A through hole 211h penetrating through the through hole line A is bored in a base end portion of the first solid electrolyte layer 211, and a through hole conductor 217 is formed on an inner peripheral surface of the through hole 211h. The through hole conductor 217 is formed integrally with a conductive portion 219 formed at a periphery of the through hole 211h in the front surface 211a of the first solid electrolyte layer 211 as well as with the connection portion 215c of the back surface 211b of the first solid electrolyte layer 211. The conductive portion 219 has a substantially-oblong shape extending in a longitudinal direction.

Likewise, the through holes of the insulation layer 231 are now described. A through hole 231$h$1 penetrating through the through hole line A is bored in a base end portion of the insulation layer 231, and a through hole conductor 233$d$ is formed on an inner peripheral surface of the through hole 231$h$1. The through hole conductor 233$d$ is formed integrally with a conductive portion 233$e$ formed at a periphery of the through hole 233$d$ within the front surface 231$a$ of the insulation layer 231 and with a conductive portion 233$f$ formed at a periphery of the through hole 233$d$ within the back surface 231$b$ of the insulation layer 231. The conductive portions 233$e$ and 233$f$ have a substantially-oblong shape extending in the longitudinal direction.

A through hole 231$h$2 penetrating through the through hole line B is bored in a base end portion of the insulation layer 231, and a through hole conductor 235$d$ is formed on an inner peripheral surface of the through hole 231$h$2. The through hole conductor 235$d$ is formed integrally with a conductive portion 235$e$ formed at a periphery of the through hole 233$d$ within the front surface 231$a$ of the insulation layer 231 and with a conductive portion 235$f$ formed at a periphery of the through hole 233$d$ within the back surface 231$b$ of the insulation layer 231. The conductive portions 235$e$ and 235$f$ have a substantially-oblong shape extending in the longitudinal direction.

The oxygen pump cell 205 will now be described.

The oxygen pump cell 205 includes a second solid electrolyte layer 221 containing a sintered partially-stabilized zirconia element, a third electrode 223$a$ formed in a leading-end side portion of a front surface 221$a$ of the second solid electrolyte layer 221, and a fourth electrode 225$a$ formed in a leading-end side portion of a back surface 221$b$ of the second solid electrolyte layer 221.

A lead portion 223$b$ and a substantially-oblong connection portion 223$c$ are integrally formed in this order from the third electrode 223$a$ toward a base end along the longitudinal direction of the gas sensing element 200. Further, a lead portion 225$b$ and a substantially-oblong connection portion 225$c$ are integrally formed in this order from the fourth electrode 225$a$ toward the base end along the longitudinal direction of the gas sensing element 200.

The fourth electrode 225$a$ is exposed to the gas measurement chamber 231$c$ of the insulation layer 231 stacked on the back surface 221$b$ of the oxygen pump cell 205.

A protective layer 241 containing alumina as a main component thereof is stacked on the front surface 221$a$ of the oxygen pump cell 205, and a porous electrode protecting portion 241$e$ is arranged in a rectangular cutout at the leading end of the protective layer 241, thereby covering the fourth electrode 223$a$. The electrode protecting portion 241$e$ inhibits poisoning of the fourth electrode 223$a$.

Thus, oxygen in the gas measurement chamber 231 is pumped by means of the third electrode 223$a$ and the fourth electrode 225$a$.

The through holes of the second solid electrolyte layer 221 will now be described. A through hole 221$h$1 penetrating through the through hole line A is bored in a base end portion of the second solid electrolyte layer 221, and a through hole conductor 226 is formed on an inner peripheral surface of the through hole 221$h$1. The through hole conductor 226 is electrically connected to a conductive portion 222 formed at a periphery of the through hole 221$h$ in the front surface 221$a$ of the second solid electrolyte layer 221 and a conductive portion 224 formed at a periphery of the through hole 221$h$ within the back surface 221$b$ of the second solid electrolyte layer 221. The conductive portions 222 and 224 each have a substantially-oblong shape extending in the longitudinal direction.

Moreover, a through hole 221$h$2 penetrating through the through hole line B is bored in the base end portion of the second solid electrolyte layer 221, and a through hole conductor 227 is formed on an inner peripheral surface of the through hole 221$h$2. The through hole conductor 227 is electrically connected a conductive portion 229 formed at a periphery of the through hole 221$h$2 within the front surface 221$a$ of the second solid electrolyte layer 221 as well as with the connection portion 225$c$ of the back surface 221$b$ of the second solid electrolyte layer 221. The conductive portion 229 has a substantially-oblong shape extending in the longitudinal direction.

Likewise, the through holes of the protective layer 241 are now described. A through hole 241$h$1 penetrating through the through hole along line A is bored in a base end portion of the protective layer 241, and a through hole conductor 271 is formed on an inner peripheral surface of the through hole 241$h$1. The through hole conductor 271 is electrically connected to a first electrode pad 243 formed at a periphery of the through hole 241$h$1 within a front surface 241$a$ of the protective layer 241 and a conductive portion 247 formed at a periphery of the through hole 241$h$1 within a back surface 241$b$ of the protective layer 241. The first electrode pad 243 has a rectangular shape larger than the through hole 241$h$1 and extends in the longitudinal direction, and the conductive portion 247 has a substantially-oblong shape extending in the longitudinal direction.

Further, a through hole 241$h$2 penetrating through the through hole along line B is bored in the base end portion of the protective layer 241, and a through hole conductor 272 is formed on an inner peripheral surface of the through hole 241$h$2. The through hole conductor 272 is electrically connected to a second electrode pad 244 formed at a periphery of the through hole 241$h$2 within the front surface 241$a$ of the protective layer 241 and a conductive portion 248 formed at a periphery of the through hole 241$h$2 within the back surface 241$b$ of the protective layer 241. The second electrode pad 244 has a rectangular shape larger than the through hole 241$h$2 and extends in the longitudinal direction, and the conductive portion 248 has a substantially-oblong shape extending in the longitudinal direction.

In addition, a through hole 241$h$3 penetrating through the through hole along line C is bored in the base end portion of the protective layer 241, and a through hole conductor 273 is formed on an inner peripheral surface of the through hole 241$h$3. The through hole conductor 273 is electrically connected to a third electrode pad 245 formed at a periphery of the through hole 241$h$3 within the front surface 241$a$ of the protective layer 241 and a conductive portion 249 formed at a periphery of the through hole 241$h$3 within the back surface 241$b$ of the protective layer 241. The third electrode pad 245 has a rectangular shape larger than the through hole 241$h$3 and extends in the longitudinal direction, and the conductive portion 249 has a substantially-oblong shape extending in the longitudinal direction.

The first electrode pad 243 is situated at a position closest to the base end side, and the second electrode pad 244 and the third electrode pad 245 are arranged at a position closer to the leading-end side than the first electrode pad 243 while being aligned to each other in a direction perpendicular to the longitudinal direction of the protective layer 241.

The heater 251 is now described. The heater 251 includes ceramic layers 253 and 255 containing alumina as a main component thereof; a heating element 257 sandwiched therebetween; and a pair of external connection pads 261 and 262 for use with a heater provided on a base end portion of a back surface 255b of the ceramic layer 255. The heating element 257 includes, in order from its leading-end side in its longitudinal direction, a heating portion 257a extending in a meandering fashion, a pair of lead portions 257b1 and 257b2, and a pair of connection portions 257c1 and 257c2. The connection portion 257c1 is electrically connected to an external connection pad 261 for use with a heater by way of a through hole 255h1 opened in a base end of the ceramic layer 255, and a connection portion 257c2 is electrically connected to an external connection pad 262 for use with a heater by way of a through hole 255h2 opened in the base end of the ceramic layer 255.

A known method can be used as the manufacturing method. For instance, conductive paste which will be used as the aforementioned various electrodes, lead portions, conductive portions, electrode pads, heating elements, and the like, is printed on front and back surfaces of each of the protective layer 241, the second solid electrolyte layer 221, the insulation layer 231, the first solid electrolyte layer 211, the ceramic layer 253, and the ceramic layer 255. Through hole conductors are formed on the respective through holes by means of through-hole plating, and the like. Subsequently, the protective layer 241, the second solid electrolyte layer 221, the insulation layer 231, the first solid electrolyte layer 211, the ceramic layer 253, and the ceramic layer 255 are stacked, and the stacked layers are sintered, whereby the gas sensing element 200 can be manufactured.

Although a material of the conductive paste is not particularly limited, a Pt-based paste exhibiting superior conductivity and corrosion resistance is preferable. Further, when an expensive material such as a Pt-based paste is used, the present embodiment is particularly effective.

An insulation layer containing alumina, titania, spinel, or the like, may be used for the protective layer 241, the insulation layer 231, and the ceramic layers 253 and 255. A solid electrolyte layer containing, for example, zirconia is used for the first solid electrolyte layer 211 and the second solid electrolyte layer 221. Accordingly, the protective layer 241 contains a first ceramic (alumina) as the first ceramic layer, and the second solid electrolyte layer 221 contains a second ceramic (zirconia) as the second ceramic layer. In such a case, the first ceramic and the second ceramic contain different materials, which may induce a decrease in adhesion between the first and second ceramic layers. However, adhesion between the first and second ceramic layers can be enhanced according to this embodiment.

A cross-sectional configuration of the through hole along line A is now described by reference to FIG. 3. The through hole along line A passes through the through holes 211h, 231h1, 221h1 and 241h1 which are concentrically arranged. Although the through holes 211h, 221h1 and 241h1 have a cylindrical shape of the same diameter, the through hole 231h1 has an oblong, cylindrical shape that is larger in diameter than the other through holes. Hence, a sidewall of the through hole 231h1 protrudes sideward from the through hole line A.

The through hole conductors 217, 226 and 271 formed on the respective through holes 211h, 221h1 and 241h1 extend outward from the edges of the respective through holes formed in the front and back surfaces around the respective through holes 211h, 221h1 and 241h1. The conductive portions 219, 224, 222 and 247 connected to the respective through hole conductors 217, 226 and 271 are formed only on the leading-end sides of the respective through holes 211h, 221h1 and 241h1.

The through hole conductive portion 233d formed on the through hole 231h1 is formed only on a front half of the through hole 231h1 on its leading-end side. The conductor 233f extends toward the inside of the through hole 233d and is connected to the conductive portion 219. Further, a conductor 233e extends in a direction opposite the through hole 233d and is connected to the conductive portion 224.

Further, the first electrode pad 243 is formed only on the leading-end side portion of the through hole 241h1.

Figure 3:
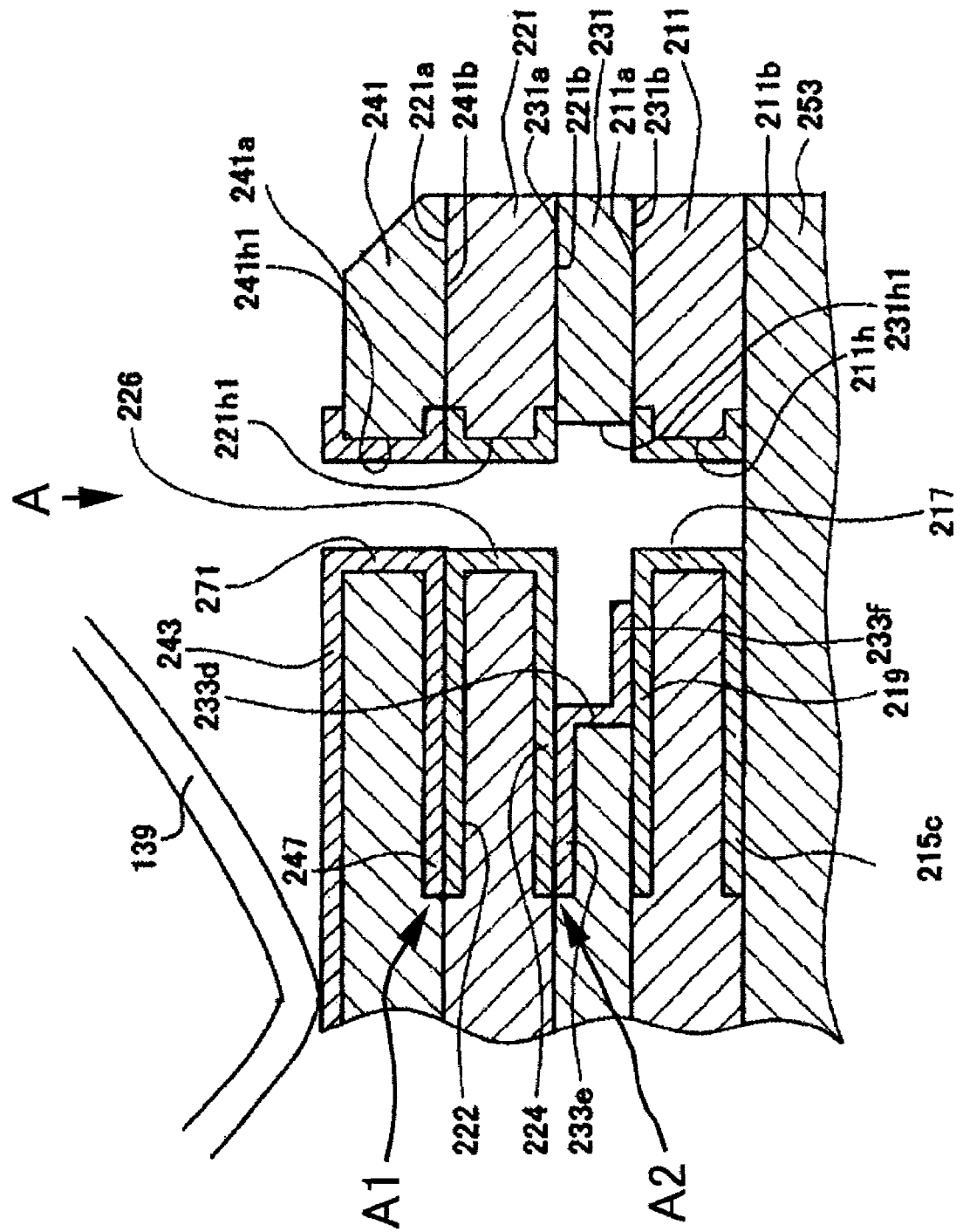
FIG. 3 is a view showing a cross-sectional configuration of a through hole along line A.

In the through hole along line A, examples of a combination of a "first conductor" with a "second conductor" include a combination of the conductor 247 with the conductor 222 (A1 in FIG. 3) and a combination of the conductor 224 with the conductor 233e (A2 in FIG. 3).

Specifically, in relation to the combination A1, the protective layer 241 is an example of a "first ceramic layer"; the second solid electrolyte layer 221 is an example of a "second ceramic layer"; the through hole 241h1 is an example of a "first through hole"; the through hole 221h1 is an example of a "second through hole"; the through hole conductor 271 is an example of a "first through hole conductor"; the through hole conductor 226 is an example of a "second through hole conductor"; the conductor 247 is an example of a "first conductor"; and the conductor 222 is an example of a "second conductor."

In relation to the combination A2, the second solid electrolyte layer 221 is an example of a "first ceramic layer"; the insulation layer 231 is an example of a "second ceramic layer"; the through hole 221h1 is an example of a "first through hole"; the through hole 231h1 is an example of a "second through hole"; the through hole conductor 226 is an example of a "first through hole conductor"; the through hole conductor 233d is an example of a "second through hole conductor"; the conductor 224 is an example of a "first conductor"; and the conductor 233e is an example of a "second conductor."

Figure 4:
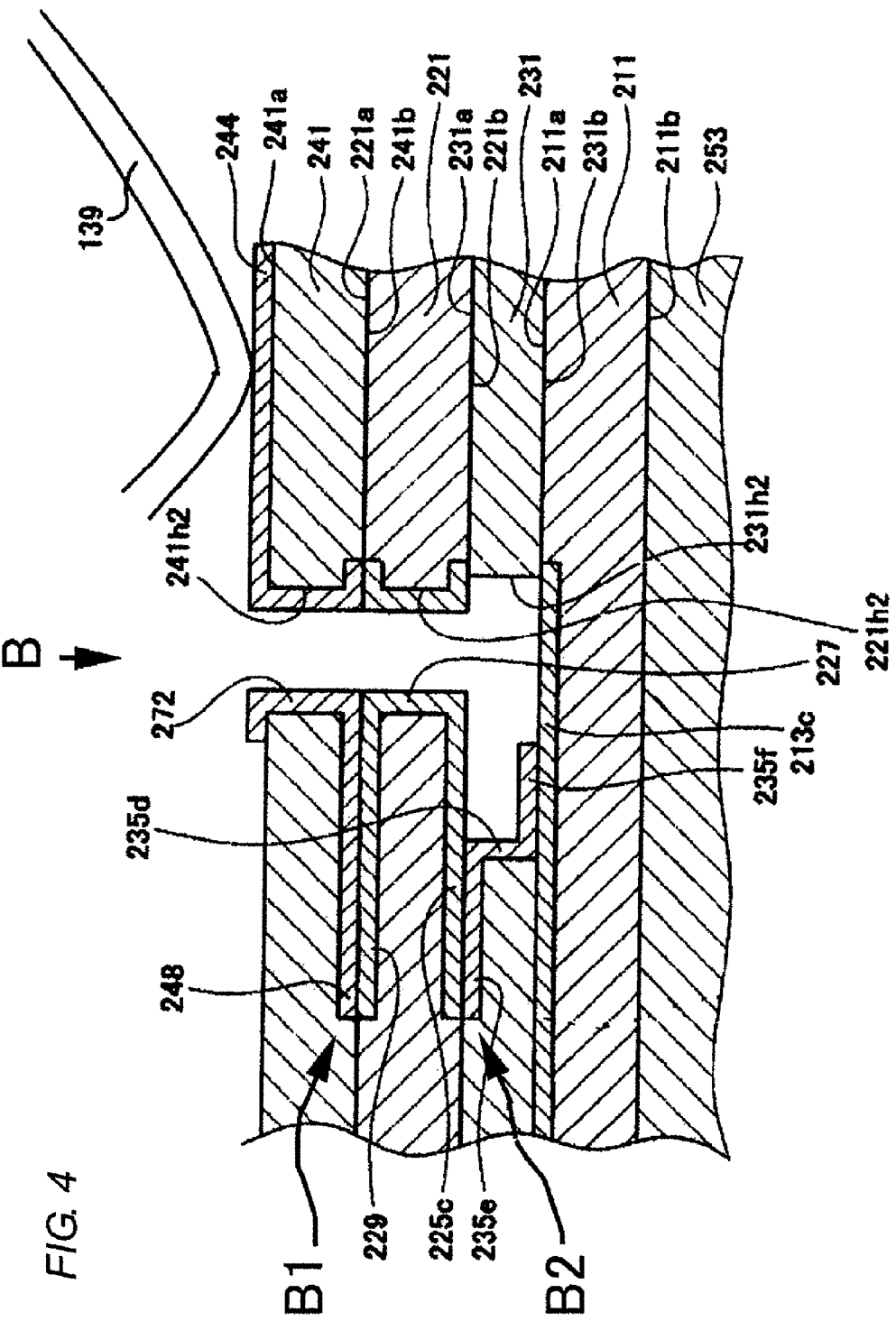
FIG. 4 is a view showing a cross-sectional configuration of a through hole along line B.

With reference to FIG. 4, a cross-sectional configuration of the through hole along line B is now described. Since the through hole along line B is substantially identical with the through hole along line A except that no through holes are formed in the first solid electrolyte layer 211, explanation thereof is omitted for brevity.

The electrode pad 244 is formed only on the base end side of the through hole 241h2. The conductive portion 235f is connected to the connection portion 213c.

In relation to the through hole along line B, examples of the combination of the "first conductor" with the "second conductor" include a combination of the conductor 248 with the conductor 229 (B1 in FIG. 4) and a combination of the conductor 225c with the conductor 235e (B2 in FIG. 4).

Specifically, in relation to the combination B1, the protective layer 241 is an example of a "first ceramic layer"; the second solid electrolyte layer 221 is an example of a "second ceramic layer"; the through hole 241h2 is an example of a "first through hole"; the through hole 221h2 is an example of a "second through hole"; the through hole conductor 272 is an example of a "first through hole conductor"; the through hole conductor 227 is an example of a "second through hole conductor"; the conductor 248 is an example of a "first conductor"; and the conductor 229 is an example of a "second conductor."

In relation to the combination B2, the second solid electrolyte layer 221 is an example of a "first ceramic layer"; the insulation layer 231 is an example of a "second ceramic layer"; the through hole 221h2 is an example of a "first through hole"; the through hole 231h2 is an example of a "second through hole"; the through hole conductor 227 is an example of a "first through hole conductor"; the through hole conductor 235*d* is an example of a "second through hole conductor"; the conductor 225*c* is an example of a "first conductor"; and the conductor 235*e* is an example of a "second conductor."

Figure 5:
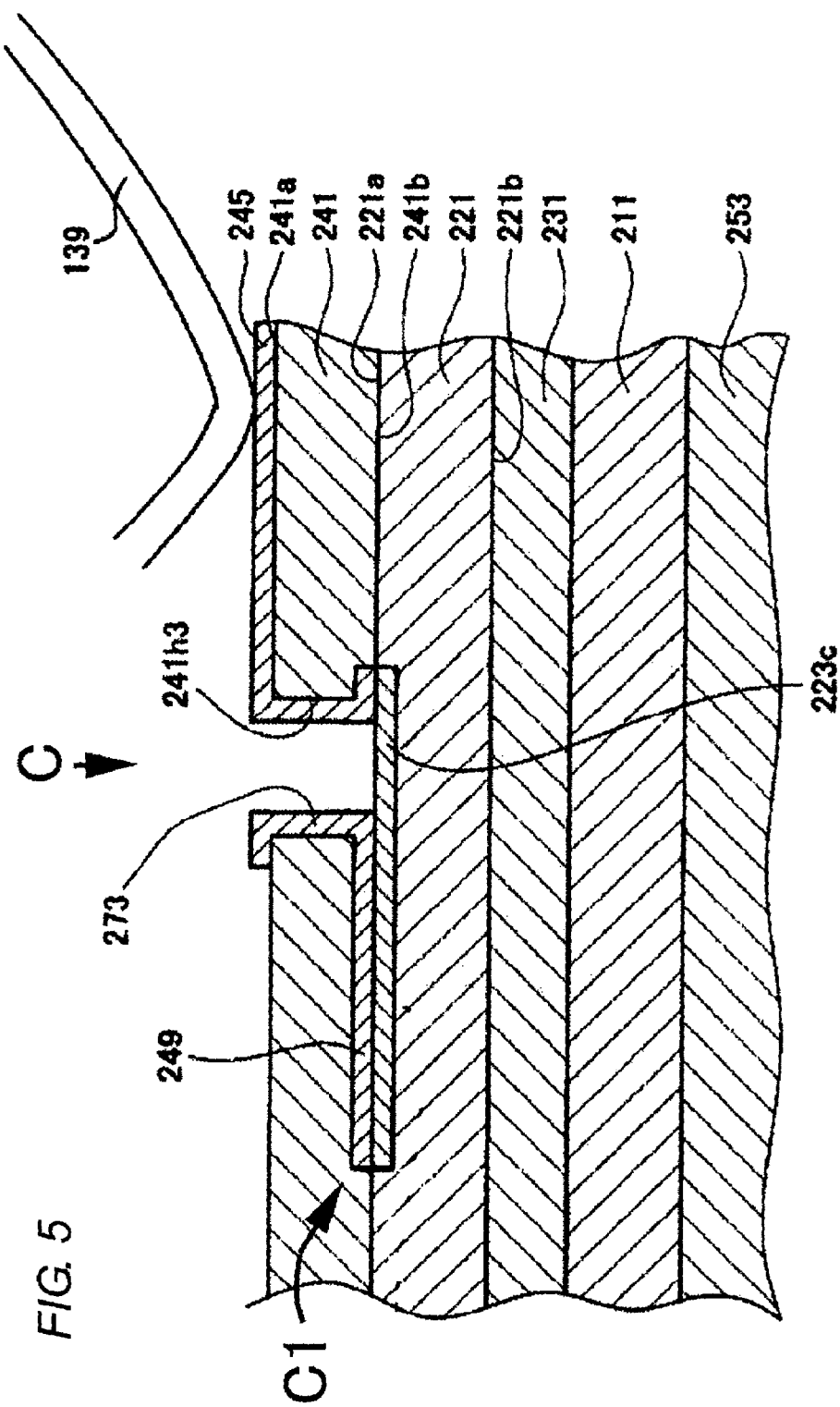
FIG. 5 is a view showing a cross-sectional configuration of a through hole along line C.

A cross-sectional configuration of the through hole along line C is now described by reference to FIG. 5. In relation to the through hole along line C, the conductor 249 connected to the through hole conductive portion 273 formed on the through hole 241*h*3 is formed only on the leading-end side of the through hole. Further, the electrode pad 245 is formed only on the base end side of the through hole 241*h*3.

In relation to the through hole along line C, a combination of the conductor 249 with the connection portion 223*c* (C1 in FIG. 5) is an example of the combination of the "first conductor" with the "second conductor".

Specifically, in relation to the combination C1, the protective layer 241 is an example of a "first ceramic layer"; the second solid electrolyte layer 221 is an example of a "second ceramic layer"; the through hole 241*h*3 is an example of a "first through hole"; the through hole conductor 273 is an example of a "first through hole conductor"; the conductor 249 is an example of a "first conductor"; and the connection portion 223*c* is an example of a "second conductor."

Configurations of the "first conductor" and the "second conductor" are now described.

Figure 6:
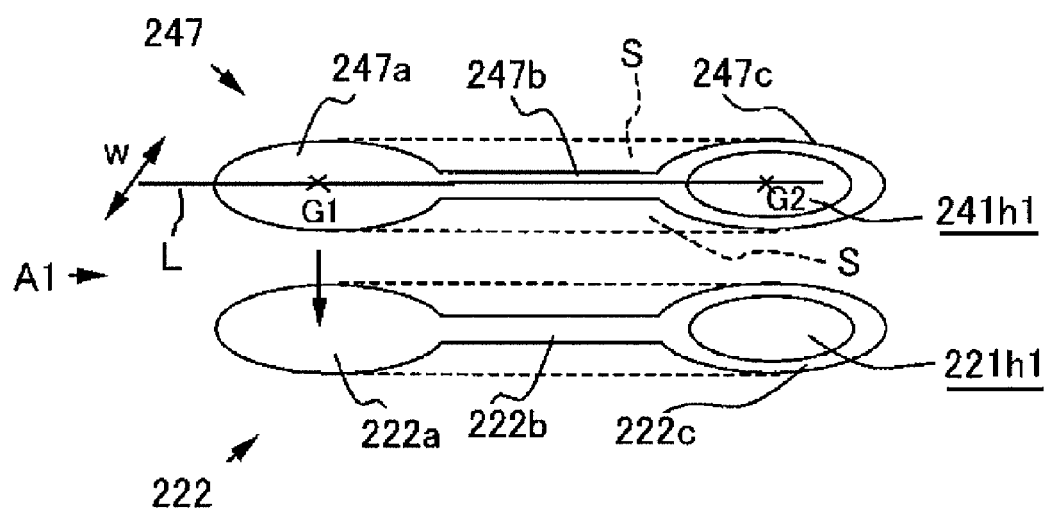
FIG. 6 is a partial perspective view showing a combination of a conductor with a conductor in the through hole along line A.

FIG. 6 is a partial-perspective view of a gas sensor of the embodiment of the present invention, showing the combination of the conductor 247 with the conductor 222 of the through hole line A (the combination A1 in FIG. 3). In addition to the combination A1, the combinations A2, B1 and B2 have configurations similar to the combination shown in FIG. 6. Detailed descriptions are hereinbelow provided only as to the combination A1, and detailed explanations of the combinations A2, B1 and B2 are omitted.

In FIG. 6, the conductor 247 as the "first conductor" includes a first peripheral conductive portion 247*c* of the through hole 241*h*1, a first lead portion 247*b* that is narrower than the first peripheral conductive portion 247*c*, and a first circular contact conductive portion 247*a* that is wider than the lead portion 247*b*, which are integrally formed in this order along the longitudinal direction. The substantially-circular first peripheral conductive portion 247*c* and the first contact conductive portion 247*a* are connected to both ends of the first elongated lead portion 247*b* having the smallest width, and the conductor 247 has a dumbbell shape as a whole. The width of the first lead portion 247*b* may be 10-90%, more preferably, 15-70% of the width of the first contact conductive portion 247*a* and/or the first peripheral conductive portion 247*c*.

The "width" of the conductor 247 herein refers to a width along a direction "w" that is perpendicular to a line L connecting a gravity point G2 of the first peripheral conductive portion 247*c* and a gravity point G1 of the first contact conductive portion 247*a*. The first lead portion 247*b* refers to a portion of the conductor 247 having the smallest width. The longitudinal direction of the conductor 247 coincides with the longitudinal direction of the protective layer 241; however, the longitudinal direction is not limited to this direction. Further, the expression "peripheral conductive portion" refers to a conductor that is provided at a periphery of a through hole on a ceramic layer and that is connected to a through hole conductor provided on the interior of the through hole.

As shown in FIG. 6, the first contact conductive portion 247*a* of the conductor 247 is electrically connected to the conductor 222 as the "second conductor." Accordingly, an essential requirement for the first lead portion 247*b* provided between the first peripheral conductive portion 247*c* and the first contact conductive portion 247*a* is to establish electrical conduction between the first peripheral conductive portion 247*c* and the first contact conductive portion 247*a*.

Therefore, so long as the first lead portion 247*b* is provided with a narrow width, the need for a conductive material for the region S outside the lead portion 247*b* can be obviated when compared with the case where the entirety of the conductor 247 is provided with a given width (as indicated by a broken line in FIG. 6). In this manner, the amount of conductive material that is used can be remarkably reduced. Since the protective layer 241 is exposed in the region S, adhesion between the protective layer 241 and its opposing second solid electrolyte layer 221 is enhanced. Moreover, the first contact conductive portion 247*a*, which is greater in area than the first peripheral conductive portion 247*c*, is provided away from the first peripheral conductive portion 247*c* of the through hole that is likely to deform during the sintering process. Consequently, the reliability of electrical connection with the conductor 222 is enhanced.

From the viewpoint of establishing electrical connection with the second conductor 222 at a position as distant as possible from the first peripheral conductive portion 247*c* of the through hole that is likely to deform during the sintering process, the length of the first lead portion 247*b* is preferably increased. However, if the first lead portion 247*b* is too long, the savings in conductive material will become smaller, and electrical resistance will increase. For these reasons, for instance, when the diameter of the first peripheral conductive portion 247*c* is set to 0.48 mm, the length of the first lead portion 247*b* is preferably set to about 0.5 to 1.35 mm (namely, the length of the first lead portion 247*b* is set to about one to three times as large as the diameter of the first peripheral conductive portion 247*c*).

In the meantime, the conductor 222 that is connected to the conductor 247 and that is an example of the "second conductor" has the same configuration as that of the conductor 247. The conductor 222 includes a second peripheral conductive portion 222*c* of the second through hole 221*h*1, a second lead portion 222*b* that is narrower than the second peripheral conductive portion 222*c*, and a circular second contact conductive portion 222*a* that is wider than the second lead portion 222*b*, which are integrally formed and arranged in this order in the longitudinal direction. Similar to the conductor 247, the width of the second lead portion 222*b* may be 10-90%, more preferably, 15-70% of the width of the second contact conductive portion 222*a* and/or the second peripheral conductive portion 222*c*.

The second contact conductive portion 222*a* of the conductor 222 and the first contact conductive portion 247*a* are electrically connected together so as to substantially overlap each other. If the second lead portion 222*b* is formed to have a narrow width, the amount of conductive material that is used can be curtailed when compared with the case where the entire conductor 222 has a constant width (as indicated by a broken line in FIG. 6). Further, since the second solid electrolyte layer 221 is exposed, adhesion between the second solid electrolyte layer and its opposing protective layer 241 is enhanced. Further, since the second contact conductive portion 222*a*, which is larger in area than the second peripheral conductive portion 222*c*, is provided at a location away from the second peripheral conductive portion 222*c* of the through hole that is susceptible to deformation during sintering. Hence, the reliability of electrical connection with the conductor 247 is enhanced, as well.

The first lead portion 247*b* and the second lead portion 222*b* remain in contact with each other. The reliability of electrical connection between the conductor 247 and the conductor 222 is also further enhanced.

Figure 7:
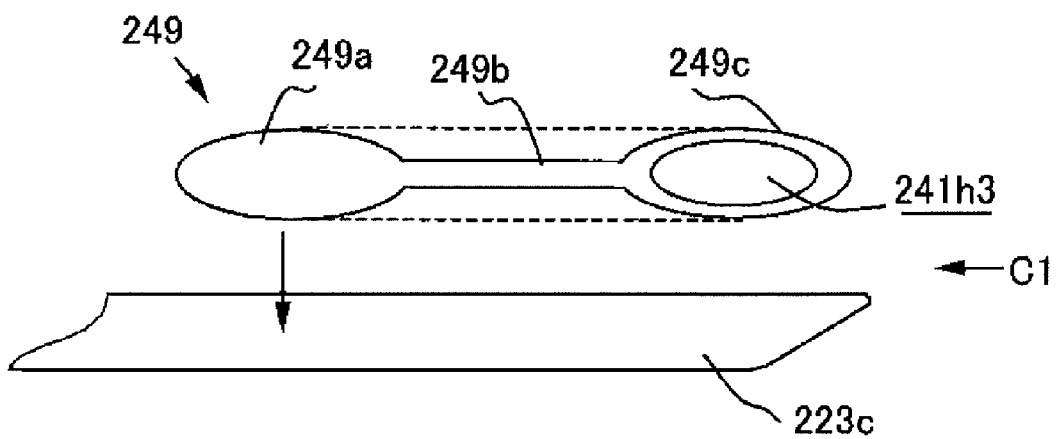
FIG. 7 is a partial perspective view showing a combination of a conductor with a conductor in the through hole along line C.

FIG. 7 is a partial-perspective view of the gas sensor of the embodiment, showing a combination of the conductor 249 with the connection portion 223c (the combination C1 shown in FIG. 5) of the through hole along line C.

In FIG. 7, the conductor 249 is an example of the "first conductor" and has the same configuration as that of the conductor 247. The conductor 249 includes a first peripheral conductive portion 249c of the through hole 241h3, a first lead portion 249b that is narrower than the first peripheral conductive portion 249c, and a first circular contact conductive portion 249a that is wider than the first lead portion 249b, which are integrally formed and arranged in this order in the longitudinal direction.

The connection portion 223c that is connected to the conductor 249 and that is an example of the "second conductor" has an elongated shape having a uniform width. The first contact conductive portion 249a of the conductor 249 and the connection portion 223c are electrically connected to each other such that the first contact conductive portion 249a overlaps a predetermined position of the connection portion 223c.

Figure 8:
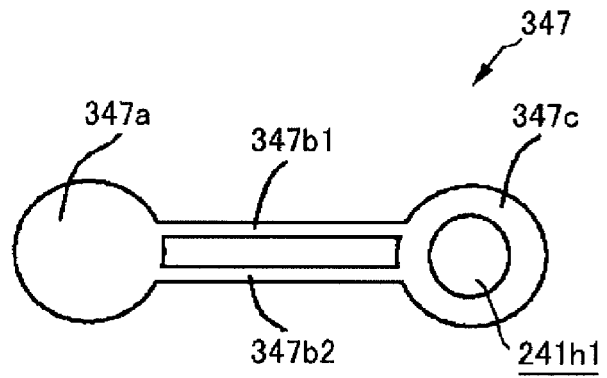
FIG. 8 is a top view showing a modification of the conductor.

FIG. 8 is a top view showing a conductor 347 serving as a modification of the conductor 247. As in the case of the conductor 247, the conductor 347 includes a first peripheral conductive portion 347c of the through hole 241h1, first lead portions 347b1 and 347b2, and a first circular contact conductive portion 347a, which are integrally formed and arranged in this order in the longitudinal direction. The conductor 347 includes two first lead portions 347b1 and 347b2. The first lead portions 347b1 and 347b2 are arranged side by side while being spaced away from each other and extend along the longitudinal direction of the conductor 247. The ends of each of the first lead portions 347b1 and 347b2 are integrally connected to the first peripheral conductive portion 347c and the first contact conductive portion 347a, respectively. When the first lead portions include two or more leads (in FIG. 8, two first lead portions 347b1 and 347b2), a total of width of all of the first lead portions is defined as the "width of the first lead portion." In the conductor 347, the width of the first lead portions 347b1 and 347b2 is the smallest among the widths present in the conductor 347.

As in the case of the conductor 347, when a plurality of lead portions are provided, even if one of the lead portions is broken, the electrical conduction will be maintained by another other lead portions. Consequently, the reliability of the electrical conduction is further enhanced. The modification shown in FIG. 8 is not limited to the first conductor but can also be applied to the second conductor.

Figure 9:
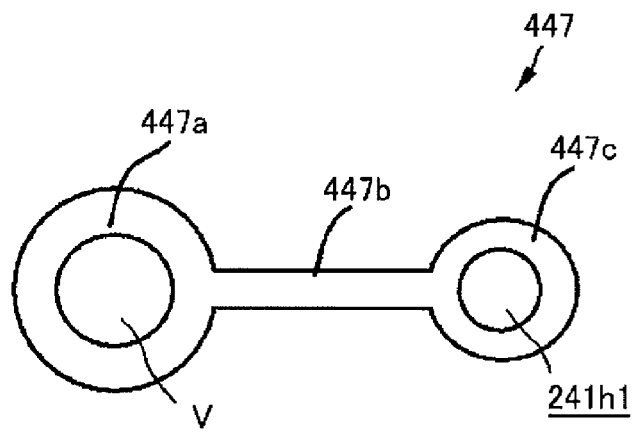
FIG. 9 is a top view showing another modification of the conductor.

FIG. 9 is a top view showing a conductor 447 according to a modification of the conductor 247. As in the case of the conductor 247, the conductor 447 includes a first peripheral conductive portion 447c of the first through hole 241h1, a first lead portion 447b, and a first circular contact conductive portion 447a, which are integrally formed in this order in the longitudinal direction.

In the conductor 447, a circular region V with no conductive material is present at the interior center of the first contact conductive portion 447a. Specifically, the first contact conductive portion 447a is formed to have an annular shape. With such a shape, even when the same amount of conductive material is used for the first contact conductive portion 447a, the outer shape of the first contact conductive portion 447a can be formed larger. Therefore, even when slight misalignment occurs at the stacking process of the ceramic layers, the first contact conductive portion 447a can reliably contact its opposing conductor. The modification shown in FIG. 9 is not limited to the first conductor and can also be applied to the second conductor.

In the present embodiment, when the first contact conductive portion and/or the second contact conductive portion have a "loop shape," the loop shape is not limited to an annular shape and may also be a loop having an outer shape; for instance, a rectangular shape, a polygonal shape, an oval shape, an indefinite shape, and the like.

Figure 10:
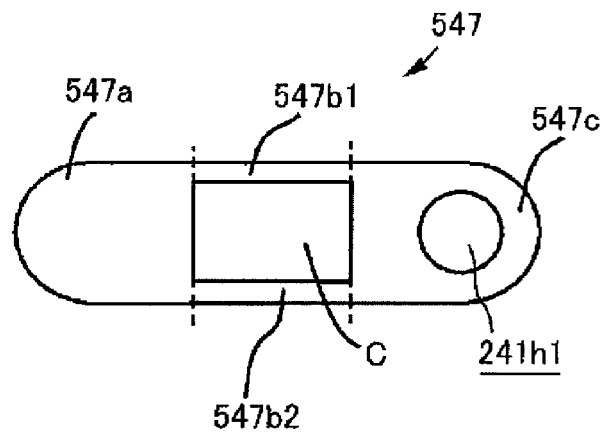
FIG. 10 is a top view showing yet another modification of the conductor.
Figure 11:
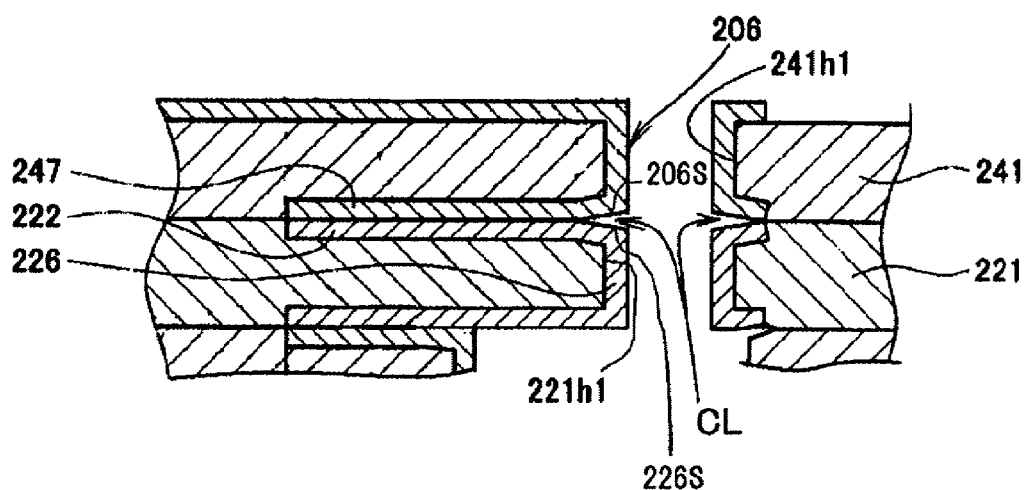
FIG. 11 is a view showing deformation, such as warpage, in a peripheral conductor upon sintering and a resulting clearance formed between the peripheral conductor and an opposing material.

FIG. 10 is a top view showing a conductor 547 according to a modification of the conductor 247. As in the case of the conductor 247, the conductor 547 includes a first peripheral conductive portion 547c of the first through hole 241h1, first lead portions 547b1 and 547b2, and a first circular contact conductive portion 547a, which are integrally formed in this order in the longitudinal direction. The conductor 547 as a whole has a shape elongated in a direction in which the first peripheral conductive portion 547c and the first contact conductive portion 547a are connected together, and a rectangular void C is formed in the center of the conductor 547. Therefore, the two sides of the void C extending along the longitudinal direction of the conductor 547 define the two first lead portions 547b1 and 547b2, respectively. Also in the case of the conductor 547, a total width of the two first lead portions 547b1 and 547b2 is defined as the "width of the lead portion."

In order to define a portion having the smallest width as a lead portion (as indicated by a broken line in FIG. 10), in a case in which the conductor 547 has an oblong shape, each of the first peripheral conductive portion 547c and the first contact conductive portion 547a has a shape that is a combination of a rectangular and a partial circle.

In the conductor 547, when a plurality of lead are provided, if one of the lead portions is broken, the electrical conduction will be maintained by another of the lead portions. Therefore, the reliability of the electrical conduction is further enhanced. Further, in the case of the conductor 547, an overall outer shape of the conductor is oblong and simpler in shape than a dumbbell shape. Hence, a printing process performed when the conductor is subjected to paste printing become easy. Further, since the outer shape of the conductor has no projections or the like, breakage, fractures and the like in the conductor will be reduced. The modification shown in FIG. 10 is not limited to the first conductor and can also be applied to the second conductor.

The present invention is not limited to the above-described embodiment and covers various modifications, equivalents, and the like, without departing from the scope and concept of the present invention. For instance, the gas sensor may be an oxygen sensor, an air-fuel sensor, a NOx sensor, a $CO_2$ sensor, and the like. Further, no specific limitations are imposed on the overall shape of the conductor, the shape of the peripheral conductive portion, the shape of the lead portion, and the shape of the contact conductive portion.

It should further be apparent to those skilled in the art that various changes in form and detail of the invention as shown and described above may be made. It is intended that such changes be included within the spirit and scope of the claims appended hereto.

This application is based on Japanese Patent Application No. 2008-175374 filed Jul. 4, 2008 and Japanese Patent Application No. 2009-105826 filed Apr. 24, 2009, the above application incorporated herein by reference in their entirety.

What is claimed is:

1. A gas sensor comprising:
a plate-shaped gas sensing element extending in a longitudinal direction and comprising a sensing portion provided at a leading-end side in the longitudinal direction, the gas sensing element comprising a plurality of stacked ceramic layers including a first ceramic layer having a first surface and a second ceramic layer having a second surface opposing the first surface, wherein the first ceramic layer has a first through hole, a first through hole conductor covering at least an inner surface of the first through hole, wherein the first ceramic layer comprises a first conductor formed on the first surface thereof, wherein the first conductor comprises: a first peripheral conductive portion provided at a periphery of the first through hole and electrically connected to the first through hole conductor; a first lead portion that is narrower than the first peripheral conductive portion; and a first contact conductive portion that is wider than the first lead portion, wherein the first peripheral conductive portion, the first lead portion and the first contact conductive portion are integrally formed and arranged in this order in the longitudinal direction, and wherein the second ceramic layer comprises a second conductor formed on the second surface thereof and electrically connected to at least the first contact conductive portion.

2. The gas sensor according to claim 1, wherein the first lead portion comprises a plurality of separated conductors extending in the longitudinal direction and electrically connecting the first peripheral conductive portion and the first contact conductive portion.

3. The gas sensor according to claim 1, wherein the first contact conductive portion has a loop shape.

4. The gas sensor according to claim 1, wherein the first contact conductive portion has an area larger than that of the first peripheral conductive portion.

5. The gas sensor according to claim 1, wherein the second ceramic layer has a second through hole with a second through hole conductor covering at least an inner surface of the second through hole, the second through hole being connected to the first through hole, wherein the second conductor comprises: a second peripheral conductive portion provided at a periphery of the second through hole and electrically connected to the second through hole conductor; a second lead portion that is narrower than the second peripheral conductive portion; and a second contact conductive portion that is wider than the second lead portion, wherein the second peripheral conductive portion, the second lead portion and the second contact conductive portion are integrally formed and arranged in this order in the longitudinal direction, and wherein at least the first contact conductive portion and the second contact conductive portion are electrically connected to each other.

6. The gas sensor according to claim 5, wherein the second lead portion comprises a plurality of separated conductors extending in the longitudinal direction and electrically connecting the second peripheral conductive portion and the second contact conductive portion.

7. The gas sensor according to claim 5, wherein the second contact conductive portion has a loop shape.

8. The gas sensor according to claim 5, wherein the second contact conductive portion has an area larger than that of the second peripheral conductive portion.

9. The gas sensor according to claim 1, wherein the first ceramic layer contains a first ceramic as a main component, and the second ceramic layer contains a second ceramic as a main component which is different from the first ceramic.

* * * * *